United States Patent
Goutsis et al.

(10) Patent No.: US 10,092,501 B2
(45) Date of Patent: Oct. 9, 2018

(54) TEMPORARY CHANGING THE COLOR OF HAIR USING PIGMENTS, ALCOHOLS AND SPECIFIC POLYALKOXYLATED SILICONES

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/492,849

(22) Filed: Apr. 20, 2017

(65) Prior Publication Data

US 2017/0216193 A1 Aug. 3, 2017

Related U.S. Application Data

(63) Continuation of application No. PCT/EP2015/071465, filed on Sep. 18, 2015.

(30) Foreign Application Priority Data

Oct. 23, 2014 (DE) .................. 10 2014 221 536

(51) Int. Cl.
| | |
|---|---|
| *A61Q 5/10* | (2006.01) |
| *A61K 8/894* | (2006.01) |
| *A61Q 5/06* | (2006.01) |
| *A61K 8/34* | (2006.01) |
| *A61K 8/29* | (2006.01) |
| *A61K 8/25* | (2006.01) |
| *A61K 8/19* | (2006.01) |

(52) U.S. Cl.
CPC ............... *A61K 8/894* (2013.01); *A61K 8/19* (2013.01); *A61K 8/25* (2013.01); *A61K 8/29* (2013.01); *A61K 8/345* (2013.01); *A61Q 5/065* (2013.01); *A61K 2800/43* (2013.01)

(58) Field of Classification Search
CPC . A61K 8/894; A61K 8/29; A61K 8/25; A61K 8/19; A61K 2800/43; A61K 8/345; A61Q 5/065

See application file for complete search history.

(56) References Cited

U.S. PATENT DOCUMENTS

| | | | |
|---|---|---|---|
| 4,983,377 A | 1/1991 | Murphy et al. | |
| 6,328,950 B1 | 12/2001 | Franzke et al. | |
| 2005/0002976 A1* | 1/2005 | Wu | A61K 8/06 424/401 |
| 2007/0009467 A1* | 1/2007 | Keller | A61K 8/044 424/70.12 |
| 2009/0119851 A1 | 5/2009 | Steigerwald et al. | |
| 2010/0285076 A1 | 11/2010 | Ozee et al. | |

FOREIGN PATENT DOCUMENTS

| | | |
|---|---|---|
| EP | 0172713 A2 | 2/1986 |
| EP | 1362576 A2 | 11/2003 |
| WO | 09920230 A2 | 4/1999 |
| WO | 2004112744 A1 | 12/2004 |
| WO | 2007005958 A2 | 1/2007 |
| WO | 2014146818 A1 | 9/2014 |

OTHER PUBLICATIONS

STIC Search Report dated Jul. 10, 2017.*
PCT International Search Report (PCT/EP2015/071465) dated Nov. 20, 2015.

* cited by examiner

*Primary Examiner* — Eisa B Elhilo
(74) *Attorney, Agent, or Firm* — James J. Cummings

(57) ABSTRACT

Agents for temporarily changing the color of keratinous fibers, in particular human hair, include in an aqueous cosmetic carrier—relative to the total weight of the agent—(a) at least 20 wt % one or more aliphatic and/or aromatic alcohols having 2 to 8 C atoms, (b) at least one color pigment and (c) at least one non-ionic polyalkoxylated silicone, wherein the total amount of the fatty substances (d) included in the agent is at a value below 2.5 wt %.

6 Claims, No Drawings

TEMPORARY CHANGING THE COLOR OF HAIR USING PIGMENTS, ALCOHOLS AND SPECIFIC POLYALKOXYLATED SILICONES

FIELD OF THE INVENTION

The present invention generally relates to a means for temporarily changing the color of keratinous fibers, in particular human hair. The present invention also relates to a method for changing the color of and styling hair, wherein a corresponding agent is sprayed onto the hair and the hair is simultaneously set in the hairstyle.

BACKGROUND OF THE INVENTION

Changing the shape and color of keratinous fibers, in particular hair, represents an important area of modern cosmetics. To change the color of hair, a person skilled in the art knows of diverse dye systems, depending on the requirements for the dyeing. For permanent, intensive dyeing with favorable fastness properties and favorable gray coverage, oxidation dyes are commonly used. Such coloring agents customarily include oxidation dye precursors, so-called developer components and coupler components, which form the actual dyes with one another under the influence of oxidizing agents, e.g., hydrogen peroxide. Oxidation dyes are characterized by very long-lasting dyeing results.

When direct dyes are used, dyes which are already formed diffuse from the dye into the hair fiber. In comparison to oxidatively dyeing hair, the coloration obtained with direct dyes exhibits a lower durability and washes away faster. Coloration with direct dyes typically lasts on the hair for a period between 5 and 20 washes of the hair.

Within the scope of modern fashion trends, there is also the need for color effects that stay on the hair for a short period of time and can then be completely removed from the hair, without leaving any residue, by washing the hair. Direct dyes diffuse more or less intensely into the hair fibers and survive there through multiple hair washes; this class of dyes is therefore not suitable for residue-free removal of the color effect.

The use of color pigments for short-term changes to the color of hair is known. "Color pigments" are generally understood to mean insoluble color-imparting substances. These remain undissolved in the form of small particles in the dye formulation; the particles attach themselves to the hair fiber only from the outside. There, they remain until the next hair wash, and can be removed by shampooing without leaving a residue behind. Under the name "hair mascara," a variety of products of this type are available on the market. Because the hair mascara can be removed by washing the hair, they are generally designed as "leave-on" products. For the user of a "leave-on" product, it is especially advantageous when he or she can also easily give a temporary shape to the hair while temporarily changing the color. Temporary shapes may entail, for example, designs such as curling, smoothing, back-combing, or form retention. Temporary shapes may be given, for example, through styling agents such as hair sprays, hair waxes, hair gels, hair fixative compositions, blow-drying, styling sprays, and the like. Temporary shaping may also be called hair styling or simply styling, and shaping agents may also be called styling agents.

Products that enable simultaneous changes to color and shape are already known from the prior art. For example, WO 9920230 A2 discloses hair mascara products that include pigments together with non-ionic polymers and high-melting waxes.

WO 2014146818 A1 discloses styling agents with pigments that are characterized by the presence of solid fatty alcohols and waxes.

The fat and wax components included in these products serve mostly to adjust to a certain drying time, through which the consumer experiences the feeling of dry hair and yet the mascara having been applied to the hair retains a residual moisture that keeps the hairstyle shapeable and combable.

Specifically with products that remain on the hair, however, there is often the problem that the hair is weighed down by the presence of the fatty components. Visually, this gives the impression of "greasy hair," and the setting properties of these products are comparatively poor. There is therefore still room for improvement with combination products for changing color and styling.

Accordingly, it is desirable to provide a versatile hair mascara product that makes it possible to temporarily change the color of hair. It should be possible to manufacture the hair mascara so that the hair mascara can be applied by means of a sponge, with a brush, and even by spray application. The change in color should be easy to perform and proceed with little damage, and should be removable from the hair by a washing, without leaving residue behind. Until the time of the next hair wash, however, the product located on the hair should be extremely resistant to external influences, i.e., neither friction against textiles nor combing should cause visible loss of color or other such detachment of the product. At the same time, the hair that has been thus dyed should have a soft grip, should not be weighed down, should not feel hard or greasy, and also visually should not give the impression of greasy hair.

Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is an agent for temporarily changing the color of keratinous fibers, in particular human hair, which include, in an aqueous cosmetic carrier, relative to the total weight of the agent,
(a) at least 20 wt % one or more aliphatic and/or aromatic alcohols having 2 to 8 C atoms,
(b) at least one color pigment, and
(c) at least one non-ionic polyalkoxylated silicone,
wherein the total amount of the fatty substances (d) included in the agent is at a value below 2.5 wt %.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been surprisingly shown that the above-discussed objectives can be solved by the use of color pigments and certain non-ionic polyethoxylated silicones when these are used in a specific aqueous-alcoholic carrier that is characterized by high alcohol content and low fatty component content.

Keratinous fibers, keratin-containing fibers, or keratin fibers are understood to mean fur, wool, feathers, and in particular human hair. Although the agents according to the present invention are primarily suited for lightening and dyeing keratin fibers, use in other fields is also possible in principle.

The term "temporarily changing the color" and related terms are understood, within the scope of the present invention, to mean a temporary coloring of the hair that can be completely or almost completely removed by washing the hair (with a commercially available shampoo). The term "temporarily changing the color," within the meaning of the present invention, does not encompass oxidative dyeing performed with oxidation dyes. The term "temporarily changing the color" also does not encompass lightening or bleaching keratin fibers or coloring the keratin fibers blond by using an oxidizing agent. The effects brought about by oxidative dyeing and brought about by blond coloring cannot be undone by a hair wash, and therefore neither of such changes in color is temporary.

The agents, in each case, include the ingredients that are essential to the present invention in an aqueous cosmetic carrier. For the purpose of temporarily changing the color and shape, such carriers may be, for example, gels or even surfactant-containing foaming solutions, e.g., shampoos, sprayable solutions, foam aerosols, or foam formulations.

As a first ingredient (a) essential to the present invention, the agents according to the present invention include at least 20 wt % one or more aliphatic and/or aromatic alcohols having 2 to 8 C atoms.

It shall be understood hereinbelow according to the present invention that the agents according to the present invention include one or more aliphatic and/or aromatic alcohols (a) having 2 to 8 C atoms in a total amount of at least 20 wt %.

Aliphatic and/or aromatic alcohols having 2 to 8 C atoms are compounds that possess 2 to 8 C atoms, are aliphatic and/or aromatic in nature, and bear one or more hydroxy groups.

The alcohols (a) within the meaning of the present invention do not bear any heteroatoms other than oxygen. They may include an ether group, but do not possess in addition any functional groups that are different from the hydroxy group (i.e., monoethanolamine, α-hydroxycarboxylic acids, dihydroxyacetone, and the like are not alcohols within the meaning of the present invention).

Suitable aliphatic alcohols are, for example, ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, and glycerol. Suitable aromatic alcohols are, for example, benzyl alcohol, phenoxyethanol, and phenylethyl alcohol.

In one embodiment, an agent according to the present invention for temporarily changing the color of keratinous fibers is characterized by including one or more alcohols (a) from the group consisting of ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, glycerol, benzyl alcohol, phenoxyethanol, and phenylethyl alcohol.

The alcohol (a) according to the present invention entails an organic solvent that contributes to dissolving the non-ionic polyalkoxylated silicone (c) and that affects the rate of film formation by the silicone (c) on the keratinous fibers after the agent has been applied. The alcohol(s) (a) is/are included in a minimum amount of 20 wt % in the agent according to the present invention.

It has turned out that this film formation then proceeds especially well and is especially uniform when the alcohol (s) is/are included in a minimum amount of at least 25.0 wt %, preferably at least 30.0 wt %, further preferably at least 35.0 wt %, still further preferably at least 40.0 wt %, and very especially preferably at least 50.0 wt % in the agent. The best results were observed with an alcohol content of at least 40 wt %. All quantities given in wt % are here in reference to the total amount of all of the alcohols (a) according to the present invention that are used in relation to the total weight of the agent.

In a preferred embodiment, an agent according to the present invention is characterized by including—relative to the total weight thereof—one or more alcohols (a) in a total amount of at least 25.0 wt %, preferably at least 30.0 wt %, further preferably at least 35.0 wt %, still further preferably at least 40.0 wt %, and very especially preferably at least 50.0 wt %.

The alcohols from the group (a) involve compounds that possess different high boiling points and different levels of volatility. It has been found that ethanol is most suitable of the members of this group. If the agents include significant amounts of ethanol, the pigments deposited on the keratin fibers are enclosed by a polymer film of the silicones (c) that is formed so that the pigments stick especially well onto the keratin fibers. In this case, the color result is especially uniform and the degradation of the pigments caused by friction on textiles is minimized.

In a very especially preferred embodiment, an agent according to the present invention is therefore characterized by including—relative to the total weight thereof—at least 30.0 wt %, preferably at least 35.0 wt %, further preferably at least 40.0 wt %, and very especially preferably at least 45.0 wt % ethanol.

The aforementioned properties can be even further improved when another polyhydric alcohol of lower volatility, e.g., 1,2-propanediol or glycerol, is added to the ethanol in a lower quantity.

In another very especially preferred embodiment, an agent according to the present invention is therefore characterized by including—relative to the total weight thereof- 1,2-propanediol and/or glycerol in a total amount of 0.1 to 7.0 wt %, preferably 0.5 to 5.5 wt %, further preferably 1.0 to 3.5 wt %, and especially preferably 1.5 to 2.5 wt %. The agents according to the present invention include all of the essential components in an aqueous carrier. The water content of the agent can also affect the deposition of the pigments on the keratin fibers and the formation of the film by the silicones (c). If the water content is too high, then there is the risk that the product will not dry sufficiently quickly. In particular, if the agents are adjusted to a lower viscosity (e.g., because they are to be sprayed), then the color result may turn out to be more uneven. In this context, it has turned out to be suitable to have a water content between 20 and 60 wt %, preferably between 24 and 54 wt %, further preferably between 28 and 50 wt %, and especially preferably between 32 and 42 wt %. The water content, given in wt %, refers here to the amount of water that is included in the total weight of the agent.

In another very especially preferred embodiment, an agent according to the present invention is therefore characterized by having—relative to the total weight thereof—a water content between 20 and 60 wt %, preferably between 24 and 54 wt %, further preferably between 28 and 50 wt %, and especially preferably between 32 and 42 wt %.

As a second component essential to the present invention, the agents include at least one color pigment (b) for temporarily changing the color. A "pigment" within the meaning of the present invention is understood to mean a dyeing compound that has a solubility of less than 0.1 g/L in water at 20° C.

The following method can be used to determine the water solubility of the pigment: 0.1 g of the pigment is weighted in a beaker. A stir bar is added. Then, the beaker is filled with distilled water (20° C.) up to 1 L. The water is stirred for 1 hour. If undissolved components of the pigment are visible in the mixture after this time, then the solubility of the pigment is below 0.1 g/L.

The agents according to the present invention are intended to produce a temporary color. Special attention is to be given here to generating "metallic" effects. Therefore, white pigments do not fall under the definition of the color pigments. White pigments are achromatic inorganic pigments having a high refractive index (idR greater than 1.8), which are generally synthetically produced and used, in particular, to generate an optical white in coating compositions or used as a filler in, for example, plastics. White pigments such as titanium oxide or zinc dioxide are explicitly not included under the definition of a color pigment.

In the agents, the color pigments are present in the form of small undissolved particles that do not diffuse into the hair fibers, but rather are deposited onto the outer wall of the keratin fibers under the influence of the silicone (c), and are held there by a polymeric silicone layer.

Suitable color pigments may be of organic and/or inorganic origin.

Due to the excellent light, water, and/or temperature resistance thereof, the use of inorganic color pigments in the method according to the present invention is especially preferred. The preferred mean particle size of the (preferably inorganic) color pigments is 0.1 μm to 1 mm, more preferably 0.5 to 750 μm and, in particular, 10 to 500 μm.

Preferred color pigments are selected from inorganic pigments that may be of synthetic or natural origin. Inorganic color pigments of natural origin may be prepared from, for example, chalk, ochre, umber, green earth, burnt sienna, or graphite. As inorganic color pigments, it is also possible to use black pigments such as, for example, iron oxide black, color pigments such as ultramarine or iron oxide red, and fluorescent or phosphorescent pigments.

Especially suitable are colored metal oxides, hydroxides, and oxide hydrates, mixed-phase pigments, sulfur-containing silicates, silicates, metal sulfides, complex metal cyanides, metal sulfates, chromates, and/or molybdates. Especially preferred color pigments are black iron oxide (Cl 77499), yellow iron oxide (Cl 77492), red and brown iron oxide (Cl 77491), manganese violet (Cl 77742), ultramarine (sodium aluminum sulfosilicates, Cl 77007, Pigment Blue 29), chromium oxide hydrate (CI77289), iron blue (Ferric Ferrocyanide, CI77510), and/or carmine (Cochineal).

Color pigments that are especially preferred according to the present invention are colored pearlescent pigments. These are commonly mica-based and may be coated with one or more metal oxides from the group consisting of titanium dioxide (Cl 77891), black iron oxide (Cl 77499), yellow iron oxide (Cl 77492), red and/or brown iron oxide (Cl 77491, Cl 77499), manganese violet (Cl 77742), ultramarine (sodium aluminum sulfosilicates, Cl 77007, Pigment Blue 29), chromium oxide hydrate (Cl 77289), chromium oxide (Cl 77288) and/or iron blue (Ferric Ferrocyanide, Cl 77510).

Mica is a type of phyllosilicate. The principal representatives of these silicates are muscovite, phlogopite, paragonite, biotite, lepidolite, and margarite. To prepare the pearlescent pigments in connection with metal oxides, the mica—mainly muscovite or phlogopite—is coated with a metal oxide.

As an alternative to natural mica, it is also possible to use synthetic mica optionally coated with one or more metal oxides as a pearlescent pigment. Such suitable natural mica-based pearlescent pigments are disclosed in patent publication WO 2005065632, incorporated herein by reference. Especially preferred pearlescent pigments are based on natural or synthetic mica and are coated with one or more of the aforementioned metal oxides. The color of the respective pigments may be varied through variation of the coating thickness of the metal oxide(s).

In another especially preferred embodiment, an agent according to the present invention is characterized by including, as the color pigment (b), at least one inorganic color pigment selected from colored metal oxides, metal hydroxides, metal oxide hydrates, silicates, metal sulfides, complex metal cyanides, metal sulfates, bronze pigments, and/or mica-based colored pigments that have been coated with at least one metal oxide and/or metal oxychloride.

In another very especially preferred embodiment, an agent according to the present invention is characterized by including, as the color pigment (b), at least one mica-based colored pigment that is coated with one or more metal oxides from the group consisting of titanium dioxide (Cl 77891), black iron oxide (Cl 77499), yellow iron oxide (Cl 77492), red and/or brown iron oxide (Cl 77491, Cl 77499), manganese violet (Cl 77742), ultramarine (sodium aluminum sulfosilicates, Cl 77007, Pigment Blue 29), chromium oxide hydrate (Cl 77289), chromium oxide (Cl 77288) and/or iron blue (Ferric Ferrocyanide, Cl 77510).

Examples of especially suitable color pigments are commercially available, for example, under the trade names Rona®, Colorona®, Dichrona®, and Timiron® from the company Merck, Ariabel® and Unipure® from the company Sensient, Prestige® from the company Eckart Cosmetic Colors, and Sunshine® from the company Sunstar. Examples of very especially preferred color pigments with the tradename Colorona® include:

Colorona Copper, Merck, MICA, Cl 77491 (IRON OXIDES)
Colorona Passion Orange, Merck, Mica, Cl 77491 (Iron Oxides), Alumina
Colorona Patina Silver, Merck, MICA, Cl 77499 (IRON OXIDES), Cl 77891 (TITANIUM DIOXIDE)
Colorona RY, Merck, Cl 77891 (TITANIUM DIOXIDE), MICA, Cl 75470 (CARMINE) Colorona Oriental Beige, Merck, MICA, Cl 77891 (TITANIUM DIOXIDE), Cl 77491 (IRON OXIDES)
Colorona Dark Blue, Merck, MICA, TITANIUM DIOXIDE, FERRIC FERROCYANIDE Colorona Chameleon, Merck, Cl 77491 (IRON OXIDES), MICA
Colorona Aborigine Amber, Merck, MICA, Cl 77499 (IRON OXIDES), Cl 77891 (TITANIUM DIOXIDE)
Colorona Blackstar Blue, Merck, Cl 77499 (IRON OXIDES), MICA
Colorona Patagonian Purple, Merck, MICA, Cl 77491 (IRON OXIDES), Cl 77891 (TITANIUM DIOXIDE), Cl 77510 (FERRIC FERROCYANIDE)

Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON Colorona Gold Plus MP 25, Merck, MICA, TITANIUM DIOXIDE (CI 77891), IRON OXIDES (CI77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, MICA, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iran oxides), Mica, CI 77891 (Titanium dioxide) Colorona Bright Gold, Merck, Mica, CI 77891 (Titanium dioxide), CI 77491 (Iron oxides) Colorona Blackstar Gold, Merck, MICA, CI 77499 (IRON OXIDES)

Examples of also especially preferred color pigments with the tradename Unipure® include:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica Depending on what color change in the keratinous fibers is desired, the color pigment(s) (b) may be used in different amounts. Generally, the more pigment is used, the higher the degree of the change in color. From a certain usage amount, however, the adherence of the pigments to the keratin fibers hits a limit value beyond which it is no longer possible to increase the extent of change in color by further increasing the amount of pigment used.

In this context, it has turned out that when the silicones (c)—in particular, the aforementioned preferred and especially preferred representatives—according to the present invention are used, a film that makes the pigments stick in especially large quantities to the keratin fibers can be formed on the keratin fibers. The agents according to the present invention may therefore include the color pigments (b) in a total amount of 1.0 to 25.0 wt %, preferably 5.0 to 20.0 wt %, further preferably 7.0 to 18.0 wt %, and especially preferably 8.5 to 15.5 wt %. In another especially preferred embodiment, an agent according to the present invention is therefore characterized by including—relative to the total weight thereof—one or more color pigments (b) in a total amount of 1.0 to 25.0 wt %, preferably 5.0 to 20.0 wt %, further preferably 7.0 to 18.0 wt %, and especially preferably 8.5 to 15.5 wt %.

As a third component (c) essential to the present invention, the agents for temporarily changing the color of keratin fibers include at least one non-ionic polyalkoxylated silicone. Silicones are polymeric compounds that are built according to the pattern (R2SiO)x, wherein R generally stands for an organic residue, often an alkyl group or even a substituted alkyl group. Silicones are also known as polyorganosiloxanes, and may be linear or branched. The silicon atoms are linked via oxygen atoms in an Si—O—Si bond.

As structural units, polyalkoxylated silicones bear polyoxyalkylene groups, in particular polyoxyethylene groups (i.e., groups of the type [—CH$_2$—CH$_2$—O-]m) and/or polyoxypropylene groups (i.e., groups of the type [—CH(CH$_3$)—CH$_2$—O-]$_m$ and/or [—CH$_2$—CH$_2$—CH$_2$—O-]$_m$). The number m of the polyoxyalkylene units in the silicone polymer is at least 2.

Polymeric compounds are understood to mean macromolecules having a molecular weight at least 1,000 g/mol, preferably at least 2,500 g/mol, especially preferably at least 5,000 g/mol, which are composed of identical repetitive organic units. The maximum molecular weight of the silicone depends on the degree of polymerization (number polymerized monomers) and the batch size, and is determined as a consequence of the method of polymerization. Within the meaning of the present invention, it is preferred when the maximum molecular weight of the silicone (c) is not more than 107 g/mol, preferably not more than 106 g/mol, and especially preferably not more than 105 g/mol.

The polyalkoxylated silicones according to the present invention entail non-ionic compounds; the silicones correspondingly bear neither positive nor negative charges.

The non-ionic silicones according to the present invention comprise structural units of the formula (a)

The structural units of formula (a) constitute the repeating units of the silicone;
the linking of two structural units of formula (a), for example, leads to formula (a')

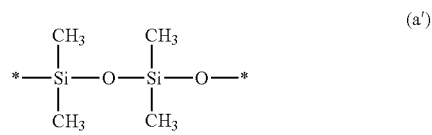

The silicones according to the present invention are furthermore polyalkoxylated and therefore comprise at least two alkylene oxide units. In a preferred embodiment, these alkylene oxide units are connected to a silicon atom via an alkylene group, especially preferably via an n-propylene group. Preferred silicones (c) accordingly comprise at least one structural unit of general formula (I)

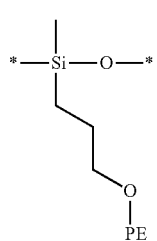

(I)

The group PE stands here for a group —$(C_2H_4O)_x$—$(C_3H_6O)_y$—H or for a group —$(C_3H_6O)_y$—$(C_2H_4O)_x$—H,
x stands for an integer from 0 to 20, and
y stands for an integer from 0 to 20,
wherein the sum of x and y is at least 2.

In another very especially preferred embodiment, an agent according to the present invention is characterized by including a non-ionic polyalkoxylated silicone (c), which comprises at least one structural unit of general formula (I),

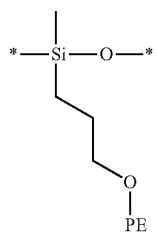

(I)

wherein
PE stands for a group —$(C_2H_4O)_x$—$(C_3H_6O)_y$—H or for a group —$(C_3H_6O)_y$—$(C_2H_4O)_x$—H,
x stands for an integer from 0 to 20,
y stands for an integer from 0 to 20, and
the sum of x and y is at least 2.

The sum of x and y is at least 2. If x stands for 1, then y stands for an integer from 1 to 20. If x stands for 2 or for an integer greater than 2, then y may also stand for 0. If y stands for 2 or for an integer greater than 2, then x may also stand for 0.

Especially preferred silicones (c) comprise, for example, the following structural units:

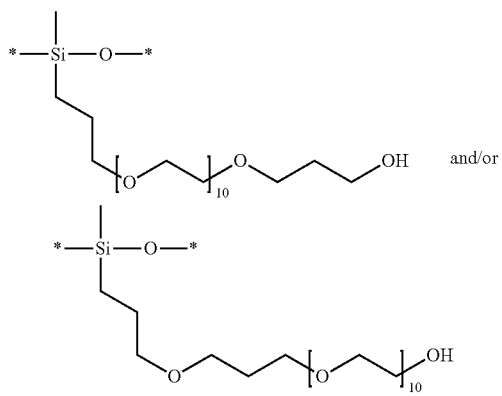

and/or

In another very especially preferred embodiment, an agent according to the present invention is characterized by including a non-ionic polyalkoxylated silicone (c), which comprises at least one structural unit of general formula (Ia),

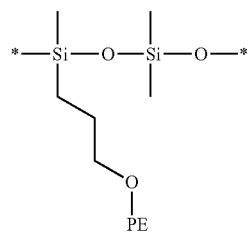

(Ia)

wherein
PE stands for a group —$(C_2H_4O)_x$—$(C_3H_6O)_y$—H or for a group —$(C_3H_6O)_y$—$(C_2H_4O)_x$—H,
x stands for an integer from 0 to 20,
y stands for an integer from 0 to 20, and
the sum of x and y is at least 2.

In a preferred embodiment, x stands for an integer from 8 to 12, and y stands for the numbers 0 or 1.

In a very especially preferred embodiment, x stands for the number 10, and y stands for the number 1.

Of very special preference is an agent for temporarily changing the color of keratinous fibers, in particular human hair, including—in an aqueous cosmetic carrier—
(a) at least 35.0 wt % ethanol
(b) at least one mica-based colored pigment that is coated with one or more metal oxides from the group consisting of titanium dioxide (Cl 77891), black iron oxide (Cl 77499), yellow iron oxide (Cl 77492), red and/or brown iron oxide (Cl 77491, Cl 77499), manganese violet (Cl 77742), ultramarine (sodium aluminum sulfosilicates, Cl 77007, Pigment Blue 29), chromium oxide hydrate (Cl 77289), chromium oxide (Cl 77288) and/or iron blue (Ferric Ferrocyanide, Cl 77510),
(c) at least one non-ionic polyalkoxylated silicone comprising at least one structural unit of general formula (I)
(d)

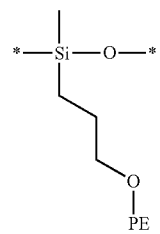

(I)

wherein
PE stands for a group —$(C_2H_4O)_x$—$(C_3H_6O)_y$—H or for a group —$(C_3H_6O)_y$—$(C_2H_4O)_x$—H,
x stands for an integer from 0 to 20,
y stands for an integer from 0 to 20, and
the sum of x and y is at least 2.

Examples of especially suitable silicones are:
Abil EM 90, from the company Evonic, CETYL PEG/PPG-10/1 DIMETHICONE
Abil EM 97 S from the company Evonic, Bis-PEG/PPG-14/14 Dimethicone Abil B 8843 from the company Evonic, PEG-14 DIMETHICONE Abil B 8851 from the company Evonic, PEG/PPG-14/4 DIMETHICONE Abil B 88183 from the company Evonic, PEG/PPG-20/6 DIMETHICONE Abil B 8863 from the company Evonic, PEG/PPG-20/20 DIMETHICONE Abil B 8852 from the company Evonic, PEG/PPG-14/12 DIMETHICONE Xiameter OFX 0193 Fluid from the company Dow Corning, PEG-12 Dimethicone Xiameter OFX 0190 Fluid from the company Dow Corning, PEG/PPG-18/18 DIMETHICONE Microcare Silicone E 1016 from the company Thor (Parka), Cetyl PEG/PPG-10/1 Dimethicone The non-ionic silicones (c) according to the present invention form, on the keratin fibers, films that lock the color pigments (b) to the keratin fibers and thus protect same against abrasion. It has turned out here that, in particular, the polyalkoxylated silicones that bear a $C_8$-$C_{40}$ alkyl group as an additional structural unit are especially suitable for forming stable films. The $C_8$-$C_{40}$ alkyl group may be linear or branched. Especially preferred polyalkoxylated silicones bear a linear $C_8$-$C_{40}$ alkyl group. Especially preferably, this $C_8$-$C_{40}$ alkyl group is present bonded to an Si atom.

In another very especially preferred embodiment, an agent according to the present invention is characterized by including a non-ionic polyalkoxylated silicone (c), which comprises at least one structural unit of general formula (II),

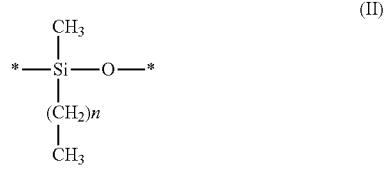

(II)

wherein n stands for an integer from 8 to 40, preferably from 10 to 30, and especially preferably from 14 to 20.

The positions marked with an asterisk may here each constitute the point of linking to another siloxane unit. The structural unit of the formula (II) may, however, also terminate the silicone. In this case, the structural unit of formula (II) constitutes the terminal group of the silicone, i.e., a position marked with an asterisk constitutes the point of connection to another siloxane unit, whereas the other position marked with an asterisk may stand for the bonding to a methyl group, a methoxy group, or a hydroxy group. Formulations that include a non-ionic polyalkoxylated silicone having at least one structural unit of formula (I) and (especially preferably) at least one structural unit of formula (II) exhibit a very finely-dispersed distribution of the color pigments (b) in the alcoholic-aqueous solution. The formulations are very favorably sprayable, and the pigments can be evenly distributed onto the keratin fibers, so that an especially homogeneous color result can be achieved.

The best results were achieved with CETYL PEG/PPG-10/1 DIMETHICONE.

In a very especially preferred embodiment, an agent according to the present invention is therefore characterized by including Cetyl PEG/PPG-10/1 Dimethicone as the non-ionic polyalkoxylated silicone (c).

The agents according to the present invention typically include the silicone(s) (c) in a total amount of 0.1 to 10.0 wt %, preferably 0.5 to 5.0 wt %, further preferably 0.8 to 3.0 wt %, and especially preferably 1.4 to 2.6 wt %. Here, the amounts given in wt % refer to the total amount of all of the non-ionic polyalkoxylated silicones (c), in relation to the total weight of the agent.

In another especially preferred embodiment, an agent according to the present invention is characterized by including—relative to the total weight thereof—one or more non-ionic polyalkoxylated silicones (c) in a total amount of 0.1 to 10.0 wt %, preferably 0.5 to 5.0 wt %, further preferably 0.8 to 3.0 wt %, and especially preferably 1.4 to 2.6 wt %.

For optimal adherence performance of the color pigments (b) onto the keratin fibers, the used amounts of pigments (b) and silicones (c) are advantageously matched to one another. If pigments (b) and silicones (c) are used in a weight ratio of 1.0 to 6.0, then most of the pigments can be effectively bound via the silicone film, and thus immobilized on the fibers. In other words, it is especially advantageous to use color pigments (b) and silicones (c) at least in equal total amounts, or, however, to choose usage amounts with which the total amount of the color pigments (b) exceeds the total amount of the silicones (c) by no more than a factor of 6. With the indicated weight ratio (b)/(c), the total amount of the pigments (b) included in the agent is set in relation to the total amount of silicones (c) included in the agent.

In another very especially preferred embodiment, an agent according to the present invention is characterized in that the weight ratio of all of the color pigments (b) included in the agent to all of the silicones (c) included in the agent—i.e., the weight ratio (b)/(c)—is a value of 1.0 to 6.0, preferably 2.0 to 5.5, further preferably 2.5 to 5.0, and especially preferably 3.0 to 4.5.

Example; A temporary dye includes 35.0 wt % water
(a) 40.0 wt % ethanol
(b) 8.0 wt % Colorona Bronze, Merck, MICA, Cl 77491 (IRON OXIDES)
(c) 2.0 wt % Cetyl PEG/PPG-10/1 Dimethicone
other ingredients up to 100 wt %
Weight ratio (b)/(c)=4.0

The hair mascara products known from the prior art generally include fatty substances; these fatty substances form a film on the keratin fibers, which protects the pigments from abrasion after use.

The main drawback of the fatty substances, however, is that they produce, on the keratin fibers, an undesirable feeling that manifests, in particular, in a sensation of hardness and greasy hair. The keratin fibers appear weighed down and also visually give the impression of greasy hair.

To prevent this shortcoming, it is a characterizing and essential feature of the agents according to the present invention that the total amount of the fatty substances (d) included in the agent is a value below 2.5 wt %, relative to the total weight of the agent. "Fatty substances" in the meaning of the present invention are understood to mean organic compounds having a solubility in water at room temperature (22° C.) and atmospheric pressure (760 mmHg) of less than 1 wt %, preferably less than 0.1 wt %. The definition of the fatty components explicitly encompasses solely uncharged (i.e., non-ionic) compounds. Charged compounds such as, for example, fatty acids and salts thereof are not understood to be fatty components. Fatty substances within the meaning of the present invention possess at least one saturated or unsaturated alkyl group having at least 12 C atoms. If the fatty substances include an unsaturated alkyl group, then it may possess one or more double bonds. The molar weight of the fatty components is at most 5,000 g/mol, preferably at most 2,500 g/mol, and especially preferably at most 1,000 g/mol. The fat components entail neither polyoxyalkylated nor polyglycerylated compounds, i.e., fatty alcohols and fatty acids that have been esterified or etherified with at least two oxyalkyl groups or with at least two glycerol units do not fall under the definition of the fatty substances.

$C_{12}$-$C_{30}$ fatty alcohols fall under the fatty substances (d). $C_{12}$-$C_{30}$ fatty alcohols are saturated, monounsaturated, or polyunsaturated linear or branched fatty alcohols having 12 to 30 C atoms. Examples of $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), and/or behenyl alcohol (docosan-1-ol). Examples of branched fatty alcohols are 2-octyl dodecanol, 2-hexyl dodecanol, and/or 2-butyl dodecanol. $C_{12}$-$C_{30}$ fatty acid triglycerides also fall under the fatty substances (d). A $C_{12}$-$C_{30}$ fatty acid triglyceride is understood to mean the triester of the trihydric alcohol glycerol with two fatty acid equivalents. Both structurally-identical and distinct fatty acids within a triglyceride molecule may be involved in the ester formations. $C_{12}$-$C_{30}$ fatty acid diglycerides also fall under the fatty substances. A $C_{12}$-$C_{30}$ fatty acid diglyceride is understood to mean the diester of the trihydric alcohol glycerol with two fatty acid equivalents. Both structurally-identical and distinct fatty acids within a diglyceride molecule may be involved in the ester formations. $C_{12}$-$C_{30}$ fatty acid monoglycerides also fall under the fatty substances. A $C_{12}$-$C_{30}$ fatty acid monoglyceride is understood to mean the monoester of the trihydric alcohol glycerol with one fatty acid equivalent.

The diesters of one ethylene glycol (1,2-ethanediol) equivalent with two fatty acid (ethylene glycol difatty acid esters) equivalents also fall under the fatty substances (d). Then, both structurally identical and different fatty acids may be involved in the ester bonds with the ethylene glycol.

Waxes also fall under the fatty substances (d). Waxes are understood to be the esters of $C_{12}$-$C_{30}$ fatty acids with $C_{12}$-$C_{30}$ fatty alcohols.

Hydrocarbons having at least 12 C atoms also fall under the fatty substances (d). Hydrocarbons are compounds that are composed exclusively of carbon and hydrogen atoms. Examples of hydrocarbons include mineral oils, liquid paraffin oils (e.g., paraffinum liquidum or paraffinum perliquidum), isoparaffin oils, semisolid paraffin oils, paraffin waxes, solid paraffin (paraffinum solidum), Vaseline, and polydecene.

Silicones are not covered by the definition of the fatty substances.

Correspondingly, the invention provides an agent for temporarily changing the color of keratinous fibers, in particular human hair, including, in an aqueous cosmetic carrier, relative to the total weight thereof,
(a) one or more aliphatic and/or aromatic alcohols having 2 to 8 C atoms in a total amount of at least 35.0 wt %,
(b) at least one color pigment, and
(c) at least one non-ionic polyalkoxylated silicone,
wherein
the total amount of the fatty substances (d) included in the agent from the group consisting of $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons is at a value below 2.5 wt %.

The use of certain raw materials makes it possible, under certain circumstances, to introduce low quantities of fatty substances into the agents according to the present invention. In order to weight the hair down as little as possible, however, it is preferable to minimize the use of the fatty substances (d) as much as possible. It is therefore preferred when the total amount of the fatty substances (d) in the agent is at a value below 2.0 wt %, preferably below 1.5 wt %, further preferably below 0.5 wt %, and especially preferably below 0.1 wt %. The amounts by weight given here refer to the total amount of all of the fatty substances (d), in relation to the total weight of the agent.

In another very especially preferred embodiment, an agent according to the present invention is therefore characterized in that the total amount of all of the fatty substances (d)—the fatty substances from the group consisting of $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons—contained in the agent is a value below 2.0 wt %, preferably below 1.5 wt %, further preferably below 0.5 wt %, and especially preferably below 0.1 wt %.

Also of special preference is an agent for temporarily changing the color of keratinous fibers, in particular human hair, including—in an aqueous cosmetic carrier—
(a) at least 35.0 wt % ethanol
(b) at least one color pigment, and
(c) at least one non-ionic polyalkoxylated silicone,
wherein
the total amount of the fatty substances (d) included in the agent from the group consisting of $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons is at a value below 0.5 wt %.

Also of very special preference is an agent for temporarily changing the color of keratinous fibers, in particular human hair, including—in an aqueous cosmetic carrier—
(a) at least 45.0 wt % ethanol
(b) at least one color pigment, and
(c) at least one non-ionic polyalkoxylated silicone,
wherein
the total amount of the fatty substances (d) included in the agent from the group consisting of $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons is at a value below 0.5 wt %.

The agents are provided as aqueous-alcoholic preparations. The silicones (c) according to the present invention are polyalkoxylated and also possess emulsifying properties. Optionally, another surface-active substance may additionally be added to the agents, such surface-active substances being called either surfactants or emulsifiers, depending on the area of use. Preferably, the agents according to the present invention additionally include at least one non-ionic surfactant and/or a cationic surfactant. The use of anionic surfactants has proven less advantageous.

The agents according to the present invention may additionally include at least one non-ionic surfactant. Alkyl polyglycosides and alkylene oxide addition products with fatty alcohols and fatty acids having (in each case) 2 to 30 mol ethylene oxide per mol fatty alcohol/fatty acid have proven to be suitable non-ionic surfactants. Preparations that have favorable properties are also obtained when they include, as non-ionic surfactants, fatty acid esters of ethoxylated glycerol that have been reacted with at least 2 mol ethylene oxide.

The non-ionic surfactants are used in amounts of 0.1 to 45 wt %, preferably 1 to 30 wt %, and very especially preferably 1 to 15 wt %, relative to the total weight of the agent.

The agents according to the present invention may additionally include at least one cationic surfactant. "Cationic surfactants" are understood to mean surfactants—i.e., surface-active compounds—that each have one or more positive charges. Cationic surfactants have exclusively positive charges. Generally, these surfactants are composed of a hydrophobic part and a hydrophilic head group, wherein the hydrophobic part is generally composed of a hydrocarbon skeleton (for example, composed of one or two linear or branched alkyl chains), and the positive charge(s) in the hydrophilic head group is/are localized. Examples of cation surfactants include quaternary ammonium compounds, which may bear one or two alkyl chains having a chain length of 8 to 28 C atoms as hydrophobic residues;

quaternary phosphonium salts, substituted with one or more alkyl chains having a chain length of 8 to 28 C atoms; or tertiary sulfonium salts.

Furthermore, the cationic charge may also be in the form of an onium structure component of a heterocyclic ring (for example, an imidazolium ring or a pyridinium ring).

In addition to the functional unit bearing the cationic charge, the cation surfactant may also include other uncharged functional groups; this is the case, for example, with Esterquats. The cationic surfactants are used in amounts of 0.1 to 45 wt %, preferably 1 to 30 wt %, and very especially preferably 1 to 15 wt %, relative to the total weight of the agent. The use of anionic surfactants has turned out to have a negative impact on the abrasion resistance of the pigments on the keratin fibers. For this reason, it is preferred to not use any anionic surfactants in the agents according to the present invention.

Anionic surfactants refer to surface-active agents having exclusively anionic charges (neutralized through a corresponding counter reaction).

Examples of anionic surfactants are fatty acids, alkylsulfates, alkyl ether sulfates, and ether carboxylic acids having 12 to 20 C atoms in the alkyl group and up to 16 glycol ether groups in the molecule. In another preferred embodiment, agents according to the present invention are characterized in that the total amount of all of the anionic surfactants included in the agent is a value below 2.5 wt %, preferably below 1.5 wt %, further preferably below 0.5 wt %, and especially preferably below 0.1 wt %—wherein all amounts given are relative to the total weight of the agent.

The agents according to the present invention may furthermore include at least one zwitterionic and/or amphoteric surfactant.

Suitable zwitterionic surfactants are betaines, N-alkyl-N, N-dimethylammonium glycinates, N-acyl aminopropyl-N, N-dimethyl ammonium glycinates, and 2-alkyl-3-carboxymethyl-3-hydroxyethyl imidazolines. A preferred zwitterionic surfactant is known under the INCI name Cocamidopropyl Betaine.

Suitable amphoteric surfactants are N-alkylglycines, N-alkylpropionic acids, N-alkylaminobutyric acids, N-alkyliminodipropionic acids, N-hydroxyethyl-N-alkyl amidopropyl glycines, N-alkyl taurines, N-alkyl sarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acyl sarcosine.

The amphoteric and/or zwitterionic surfactants are used in amounts of 0.1 to 45 wt %, preferably 1 to 30 wt %, and very especially preferably 1 to 15 wt %, relative to the total weight of the agent.

One advantage of the agents according to the present invention is the possibility of being manufactured in a large variety of forms. With application via a sponge or via a small brush, very uniform color effects and rub-fast coloration can be achieved. It is, however, also possible to produce the agents according to the present invention as a spray. In particular, as well, the coloration obtained with the spray application is characterized by a very high uniformity.

The agents according to the present invention are adjusted to a certain viscosity, depending on the selected form of application. This is usually done through the use of one or more thickeners. There are no restrictions in principle regarding these thickening agents. Both organic and purely inorganic thickening agents may be used. Suitable thickening agents include anionic synthetic polymers; cationic synthetic polymers; naturally occurring thickening agents, such as non-ionic guar gums, scleroglucan gums or xanthan gums, gum arabic, ghatti gum, karaya gum, tragacanth gum, carrageen gum, agar, carob seed meal, pectins, alginates, starch fractions and derivatives such as amylose, amylopectin and dextrins, as well as cellulose derivatives, such as for example methyl cellulose, methyl cellulose, carboxyalkyl celluloses, and hydroxyalkyl celluloses; non-ionic, fully synthetic polymers, such as polyvinyl alcohol or polyvinylpyrrolidinone; and inorganic thickening agents, in particular phyllosilicates such as for example bentonite, particularly smectites, such as montmorillonite or hectorite.

Polysaccharides, in particular polysaccharides from the group consisting of carboxy $C_1$-$C_6$ alkyl celluloses, hydroxy $C_2$-$C_8$ alkyl celluloses, alginic acids, and/or xanthan gum enable especially easy and reproducible adjustments to the viscosity of the agents.

Varying the amount of polysaccharides used makes it possible manufacture the agent both as a gel for brush or sponge application and even as a low-viscosity sprayable solution. The other formulation ingredients and the used quantities thereof need not be adapted here. This is especially advantageous for the production of the agents.

In another especially preferred embodiment, an agent according to the present invention is therefore characterized by additionally including, as a thickener, at least one polysaccharide from the group consisting of $C_1$-$C_6$ alkyl celluloses, hydroxy $C_2$-$C_8$ alkylcelluloses, alginic acids, and/or xanthan gum.

In a very especially preferred embodiment, an agent according to the present invention is characterized by additionally including, as a thickener, at least one polysaccharide from the group consisting of hydroxy $C_2$-$C_8$ alkylcelluloses.

The thickener(s) may be used in the agents according to the present invention in a total amount of 0.1 to 4.5 wt %, preferably 0.15 to 3.5 wt %, and especially preferably 0.2 to 2.0 wt %, relative to the total weight of the agent.

To adjust the pH value, the agents according to the present invention may include one or more alkalizing agents. The alkalizing agents that can be used according to the present invention to adjust the desired pH values may be selected from the group consisting of ammonia, alkanolamines, basic amino acids, and inorganic alkalizing agents such as alkali/alkaline-earth metal hydroxides, alkali/alkaline-earth metal silicates, alkali/alkaline-earth metal phosphates, and alkali/alkaline-earth metal hydrogen phosphates. To adjust the pH value, the agents according to the present invention may include one or more acids. Examples of suitable acids include organic acids such as α-hydroxycarboxylic acids or inorganic acids. Furthermore, the agents may include one or more non-ionic polymers.

Examples of suitable non-ionogenic polymers include:
vinylpyrrolidone/vinyl ester copolymers, such as are marketed under the trademark Luviskol® (BASF). Luviskol® VA 64 and Luviskol® VA 73—each vinylpyrrolidone/vinyl acetate copolymers—are also preferred non-ionic polymers.
starches and derivatives thereof, in particular, starch ethers, such as Structure® XL (National Starch), a multifunctional salt-tolerant starch;
Shellac polyvinylpyrrolidones, such as are marketed, for example, under the designation Luviskol® (BASF).

Furthermore, the agents (V) and/or (F) may include one or more polymers from the group consisting of Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69 and/or Polyquaternium-86.

The agents according to the present invention may moreover include further active agents, auxiliary substances, and additives, including for example linear cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers, and quaternized polyvinyl alcohol; zwitterionic and amphoteric polymers; anionic polymers such as polyacrylic acids or crosslinked polyacrylic acids; structuring agents such as glucose, maleic acid and lactic acid, hair-conditioning compounds such as phospholipids, for example lecithin and cephalins; perfume oils, dimethyl isosorbide and cyclodextrins; active agents to improve the fiber structure, in particular mono-, di- and oligosaccharides such as for example glucose, galactose, fructose, fruit sugars and lactose; dyes for coloring the agent; anti-dandruff active agents such as piroctone olamine, zinc omadine, and climbazole; amino acids and oligopeptides; protein hydrolyzates of animal and/or plant origin as well as those in the form of the fatty acid condensation products thereof or optionally anionically or cationically modified derivatives thereof; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudo-ceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas, and primary, secondary and tertiary phosphates; opacifiers such as latex, styrene/PVP and styrene/acrylamide copolymers, and PEG-3 distearate; propellants such as propane-butane mixtures, $N_2O$, dimethyl ether, $CO_2$, and air.

A person skilled in the art will arrive at the selection of these other substances according to the desired properties of the agents. For other optional components and the used quantities of these components, explicit reference is made to the relevant manuals that would be known to a person skilled in the art. The additional active ingredients and auxiliaries are preferably used in the agents according to the present invention in amounts of (respectively) 0.0001 to 25 wt %, in particular 0.0005 to 15 wt %, relative to the total weight of the respective agents.

The products according to the present invention may be produced, for example, in the form of a gel, a spray, an aerosol, or a pump foam. Therefore, depending on the form of use, it is preferable to fill therewith a tube, a container, a bottle, a can, a compressed receptacle, or a receptacle having a pump spray applicator.

If the product is applied in spray form, the pigments can be applied especially uniformly to the keratin fibers. Production as an aerosol or pump spray is therefore very especially preferred.

In the aforementioned preferred embodiment, the product according to the present invention comprises a compressed receptacle. Suitable compressed gas receptacles are vessels made of metal (aluminum, tinplate, tin), protected or non-shattering plastic, or glass that is coated externally with plastic, in the selection of which pressure resistance and resistance to breakage, corrosion resistance, and ease of filling, as well as aesthetic considerations, handling, imprintability, etc. play a role. Special internal protection lacquers ensure corrosion resistance with respect to the preparation included in the compressed receptacle.

If the product according to the present invention is applied via a compressed receptacle, the agents additionally include at least one propellant gas from the group consisting of propane, propene, n-butane, isobutane, isobutene, n-pentane, pentene, isopentane, isopentene, air, nitrogen, argon, $N_2O$, and/or $CO_2$.

Within this group, the permanent gases air, nitrogen, argon, $N_2O$, and/or $CO_2$ are preferred; nitrogen, argon, and/or $CO_2$ are very especially preferred.

The agents according to the present invention may furthermore be put to use in the form of a pump spray. Suitable receptacles with a pump or squeeze mechanism are, for example, commercially available from the companies Rexam SMT or Seaquist.

With use in the form of a pump spray or in the form of an aerosol spray, the user can spray the agents according to the present invention directly onto the dry hair, and thus produce the desired temporary change in color.

Here, the user may first bring his or her hairstyle into shape—for example, by combing, back-combing, or using a curling iron—and then spray on the agent according to the present invention. It is also possible to first spray on the agent according to the present invention and later or simultaneously bring the hairstyle into shape through the aforementioned methods. A second subject matter of the present invention is therefore a method for temporarily changing the color and shape of hair, in which the agent of the first subject matter of the present invention, which has been manufactured in the form of a pump spray or aerosol spray, is sprayed onto the dry hair and the hair is set into the hair style before or during the application.

What has been stated regarding the agents according to the present invention also applies, mutatis mutandis, to other preferred embodiments of the method according to the present invention.

EXAMPLES

The following formulations were produced—all quantities refer to percent by weight, unless other indicated (active substance).

1. Sponge application

|   | wt % |
|---|---|
| Stearamidopropyl dimethylamine | 1.3 |
| Lactic acid | 0.3 |
| Cetyl PEG/PPG-10/1 Dimethicone | 2.0 |
| Glycerol | 2.0 |
| Cetyl trimethyl ammonium chloride | 0.45 |
| PEG-7 glyceryl cocoate | 2.0 |
| Hydroxyethyl cellulose | 0.2 |
| Colorona Precious Gold (Merck, Mica, CI 77891 (Titanium dioxide), Silica, CI 77491 (Iron Oxides), Tin oxide) | 8.5 |
| Ethanol | 51 |
| Water | up to 100 |

The formulation was applied by means of a small sponge to a dry strand of hair (Kerling dark blond). A uniformly-dyed strand with golden highlights was obtained.

2. Brush application

|   | wt % |
|---|---|
| Stearamidopropyl dimethylamine | 1.3 |
| Lactic acid | 0.3 |
| Cetyl PEG/PPG-10/1 Dimethicone | 2.0 |
| Glycerol | 2.0 |
| Cetyl trimethyl ammonium chloride | 0.45 |
| PEG-7 glyceryl cocoate | 2.0 |
| Hydroxyethyl cellulose | 2.0 |
| Colorona Precious Gold (Merck, Mica, CI 77891 (Titanium dioxide), Silica, CI 77491 (Iron Oxides), Tin oxide) | 8.5 |
| Ethanol | 51 |
| Water | up to 100 |

The formulation was applied with a small brush to a dry strand of hair (Kerling dark blond). A uniformly-dyed strand with golden highlights was obtained.

3. Spray application

|   | wt % |
|---|---|
| Stearamidopropyl dimethylamine | 1.3 |
| Lactic acid | 0.3 |
| Cetyl PEG/PPG-10/1 Dimethicone | 2.0 |
| Glycerol | 2.0 |
| Cetyl trimethyl ammonium chloride | 0.45 |
| PEG-7 glyceryl cocoate | 2.0 |
| Colorona Precious Gold (Merck, Mica, CI 77891 (Titanium dioxide), Silica, CI 77491 (Iron Oxides), Tin oxide) | 8.5 |
| Ethanol | 51 |
| Water | up to 100 |

A pump spray atomizer was filled with the formulation and the formulation was sprayed onto a dry strand of hair (Kerling dark blond). A uniformly-dyed strand with golden highlights was obtained.

4. Determination of the pigment distribution in formulations for spray application

|   | V1 | V2 | E |
|---|---|---|---|
| Stearamidopropyl dimethylamine | 1.3 | 1.3 | 1.3 |
| Lactic acid | 0.3 | 0.3 | 0.3 |
| Cyclomethicone (85 wt %), dimethiconol (15 wt %) | 2.0 | — | — |
| Bis-Cetearyl Amodimethicone | — | 2.0 | — |
| Cetyl PEG/PPG-10/1 Dimethicone | — | — | 2.0 |
| Glycerol | 2.0 | 2.0 | 2.0 |
| Cetyl trimethyl ammonium chloride | 0.45 | 0.45 | 0.45 |
| PEG-7 glyceryl cocoate | 2.0 | 2.0 | 2.0 |
| Colorona Precious Gold (Merck, Mica, CI 77891 (Titanium dioxide), Silica, CI 77491 (Iron Oxides), Tin oxide) | 8.5 | 8.5 | 8.5 |
| Ethanol | 51 | 51 | 51 |
| Water | up to 100 | up to 100 | up to 100 |

A pump spray atomizer was filled with the formulations V1, V2, and E. Shortly before use, the pump spray atomizer was briefly shaken, and then the respective formulation was sprayed onto a strand of hair.

| V1 | V2 | V3 |
|---|---|---|
| Color pigments (Colorona Precious Gold) collected into masses; formulation not sprayable | Color pigments (Colorona Precious Gold) collected into masses; formulation not sprayable | finely-dispersed formulation, favorably sprayable, homogeneous color result with favorable abrasion resistance |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for temporarily changing the color and shape of hair comprising
   spraying an agent onto the dry hair, and
   setting hair is into an intended hair style before or during the application,
   wherein the agent, in an aqueous cosmetic carrier, relative to the total weight of the agent, comprises
   (a) at least 20 wt. % one or more aliphatic and/or aromatic alcohols having 2 to 8 C atoms,
   (b) at least one color pigment,
   (c) at least one non-ionic polyalkoxylated silicone, and
   (d) one or more fatty substances below 2.5 wt. % of the total amount of the agent, and wherein the agent has been manufactured in the form of a pump spray or aerosol spray.

2. The method of claim 1, wherein the one or more alcohols (a) are selected from the group consisting of ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, glycerol, benzyl alcohol, phenoxyethanol, and phenylethyl alcohol.

3. The method of claim 1, wherein the non-ionic polyalkoxylated silicone (c) comprises at least one structural unit of general formula (I),

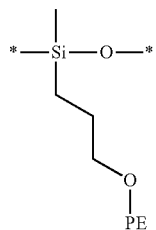

wherein PE stands for a group —$(C_2H_4O)_x$—$(C_3H_6O)_y$—H or for a group —$(C_3H_6O)_y$—$(C_2H_4O)_x$—H, in which x stands for an integer from 0 to 20, y stands for an integer from 0 to 20, and the sum of x and y is at least 2.

4. The method of claim 1, wherein the non-ionic polyalkoxylated silicone (c), comprises at least one structural unit of general formula (II),

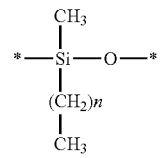

wherein n stands for an integer from 8 to 40.

5. The method of claim 1, wherein the non-ionic polyalkoxylated silicone (c) comprises cetyl PEG/PPG-10/1 dimethicone.

6. The method of claim 1, wherein the color pigment (b) comprises at least one inorganic color pigment selected from the group consisting of colored metal oxides, metal hydroxides, metal oxide hydrates, silicates, metal sulfides, complex metal cyanides, metal sulfates, bronze pigments, and mica-based colored pigments that have been coated with at least one metal oxide and/or metal oxychloride.

* * * * *